US00PP22147P2

(12) United States Plant Patent
Li

(10) Patent No.: US PP22,147 P2
(45) Date of Patent: Sep. 13, 2011

(54) ***VERBENA* PLANT NAMED 'KLEVP09390'**

(50) Latin Name: *Verbena×Hybrida*
Varietal Denomination: KLEVP09390

(75) Inventor: Ruijun Li, North Parramata (AU)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 12/798,204

(22) Filed: Mar. 31, 2010

(51) Int. Cl.
*A01H 5/00* (2006.01)

(52) U.S. Cl. ..... Plt./308

(58) Field of Classification Search ..... Plt./308
See application file for complete search history.

*Primary Examiner* — Susan McCormick Ewoldt

(74) *Attorney, Agent, or Firm* — Jondle & Associates, P.C.

(57) ABSTRACT

A new variety of *Verbena* named 'KLEVP09390' particularly characterized by large flowers, an early flowering time, and good branching, is disclosed.

1 Drawing Sheet

Genus and species: *Verbena×Hybrida.*
Variety denomination: 'KLEVP09390'.

BACKGROUND OF THE NEW PLANT

The present invention comprises a new and distinct variety of *Verbena*, botanically known as *Verbena×Hybrida*, and hereinafter referred to by the variety name 'KLEVP09390'. 'KLEVP09390' was discovered as a seedling resulting from a cross conducted in December 2005 in Cobbitty, New South Wales, Australia between the proprietary female *Verbena* parent, '04.05.100' (unpatented) and the proprietary male *Verbena* parent, '04.10.01' (unpatented). A single plant selection was subsequently chosen for further evaluation and for asexual propagation.

The new variety was first propagated via vegetative cuttings in December 2005 in Cobbitty, New South Wales, Australia, and has been asexually reproduced repeatedly by vegetative cuttings. 'KLEVP09390' has been found to retain its distinctive characteristics through successive asexual propagations via vegetative cuttings.

Plant Breeder's Rights for this variety have not been applied for. 'KLEVP09390' has not been made publicly available or sold more than one year prior to filing of this application.

SUMMARY OF THE INVENTION

The following are the most outstanding and distinguishing characteristics of this new variety when grown under normal commercial practices in a greenhouse in Stuttgart, Germany.

1. Large flowers;
2. An early flowering time; and
3. Good branching.

DESCRIPTION OF THE PHOTOGRAPH

This new *Verbena* plant is illustrated by the accompanying photograph which shows inflorescences and foliage of the plant. The colors shown are as true as can be reasonably obtained by conventional photographic procedures. The photograph was taken in Spring 2009 of a 12-week-old plant grown from rooted cuttings in a 12 centimeter pot and in a greenhouse (glasshouse) in Stuttgart, Germany under conditions which approximate those generally used in commercial practice.

DESCRIPTION OF THE NEW VARIETY

The following detailed descriptions set forth the distinctive characteristics of 'KLEVP09390'. The data which define these characteristics were collected from asexual reproductions carried out in Stuttgart, Germany. The plant history was taken on 12-week-old plants in 12 centimeter pots that were pinched once at week 10 and grown in a greenhouse. The color readings were determined under natural light. Color references are to The R.H.S. Colour Chart of The Royal Horticultural Society of London (R.H.S.), Fifth Edition (2007).

DETAILED BOTANICAL DESCRIPTION OF THE NEW PLANT

Classification:
- *Family.*—Verbenaceae.
- *Genus and species.*—*Verbena×Hybrida.*
- *Common name.*—*Verbena.*

Parentage:
- *Female parent.*—The proprietary female *Verbena* plant, '04.05.100' (unpatented).
- *Male parent.*—The proprietary male *Verbena* plant, '04.10.01' (unpatented).

Plant:
- *Form.*—Semi-trailing.
- *Growth habit.*—Compact to medium.
- *Branching habit.*—Center branching.
- *Height (from top of soil).*—Approximately 15.0 cm.
- *Width (horizontal plant diameter).*—Approximately 30.0 cm.
- *Time to produce a finished flowering plant.*—Approximately 8 to 10 weeks.
- *Time to initiate and develop roots.*—2 weeks.
- *Root description.*—White with normal structure.

Stems:
- *Number of branches per plant.*—Approximately 10.
- *Length.*—Approximately 15.0 cm.

*Diameter per branch* (*measured from the midpoint*).—Approximately 0.2 cm.
*Internode length.*—Approximately 3.0 cm.
*Color.*—RHS 139C.
*Anthocyanin.*—Absent.
*Texture.*—Velvet, hairy (pubescent).

Leaves:
*Arrangement.*—Opposite.
*Color.*—Immature and mature leaves (both upper and lower surfaces): RHS 141B.
*Length.*—3.0 cm.
*Width.*—2.0 cm.
*Shape.*—Chrysanthemum leaf-shaped.
*Apex.*—Obtuse.
*Base.*—Cordate.
*Margin.*—Serrate.
*Texture.*—Ripped.
*Venation.*—Pinnate.
*Venation color.*—RHS 141B.
*Petioles.*—Length: Approximately 1.0 cm to 2.0 cm. Diameter: 1.0 cm. Color: RHS 141B. Texture: Ripped.

Flower buds:
*Shape.*—Tall, cylindrical.
*Length.*—Approximately 1.0 cm.
*Diameter.*—Less than 0.1 cm.
*Color* (*at tight bud*).—RHS 139C.

Inflorescence:
*Blooming habit* (*flowering season*), *middle Europe.*—April to November.
*Lastingness of individual blooms on the plant.*—Approximately 2 weeks.
*Fragrance.*—Absent.
*Inflorescence type.*—Umbel.
*Length of inflorescence.*—Approximately 4.0 cm.
*Diameter of inflorescence.*—Approximately 5.0 cm.
*Number of florets per inflorescence.*—Approximately 20.
*Peduncle.*—Length: Approximately 2.0 cm. Diameter: Approximately 2.5 cm. Color: RHS 155D. Texture: Smooth.

Florets:
*Form.*—Single.
*Length.*—Approximately 2.0 cm.
*Diameter.*—Approximately 2.5 cm.
*Color.*—Immature and mature flowers (both upper and lower surfaces): RHS 155D.
*Corolla tube length.*—Approximately 1.0 cm.
*Corolla tube color.*—RHS 139C.
*Petals.*—Length of lobe: Approximately 4.0 cm. Diameter of lobe: Approximately 1.0 cm. Lobe shape: Ivy-shaped. Apex: Obtuse. Base: Acute. Margin: Serrate.
*Pedicels.*—Length: Approximately 3.0 cm. Diameter: Approximately 0.1 cm. Color: RHS 139C. Texture: Hairy (pubescent).

Calyx:
*Arrangement.*—Umbel.
*Sepals.*—Shape: Funnel. Length: Approximately 1.0 cm. Diameter: Less than 0.1 cm. Color: RHS 139C. Apex: Sinuate. Base: Acute. Margin: Sinuate. Texture: Hairy (pubescent).

Reproductive organs:
*Stamens.*—Quantity: 5. Shape: Lanceolate. Color: RHS 2D. Filament length: Less than 0.1 cm. Filament diameter: Less than 0.1 cm.
*Anther.*—Shape: Lanceolate. Color: RHS 2D. Length: Less than 0.1 cm. Diameter: Less than 0.1 cm.
*Pollen.*—Color: RHS 2D. Amount: Sparse.
*Pistils.*—Number: 1. Length: 0.1 cm. Diameter: Less than 0.1 cm. Stigma: Color: RHS 2D. Shape: Filamentous. Length: Less than 0.1 cm. Diameter: Less than 0.1 cm. Style: Color: RHS 2D. Length: Less than 0.1 cm. Diameter: Less than 0.1 cm.

Fruit and seed set: Seed length: Approximately 0.5 cm; Seed diameter: Less than 0.1 cm; Seed color: RHS 139C.

Disease, insect resistance, and physiological stress: Resistance to powdery mildew. No particular resistance to insects observed.

COMPARISON WITH PARENTAL AND COMMERCIAL VARIETIES

'KLEVP09390' differs from the female parent, the proprietary *Verbena* '04.05.100' (unpatented) in that 'KLEVP09390' has larger flowers than '04.05.100'.

'KLEVP09390' differs from the male parent, the proprietary *Verbena* '04.10.01' (unpatented) in that 'KLEVP09390' has better branching than '04.10.01'.

'KLEVP09390' differs from the commercial comparison variety 'Dümmen Empress White' (patent pending) in that 'KLEVP09390' has larger flowers than 'Dümmen Empress White'.

'KLEVP09390' differs from the commercial comparison variety 'Ball Aztek White' (patent status unknown) in that 'KLEVP09390' has better branching than 'Ball Aztek White'.

I claim:

1. A new and distinct variety of *Verbena* plant named 'KLEVP09390' as shown and described herein.

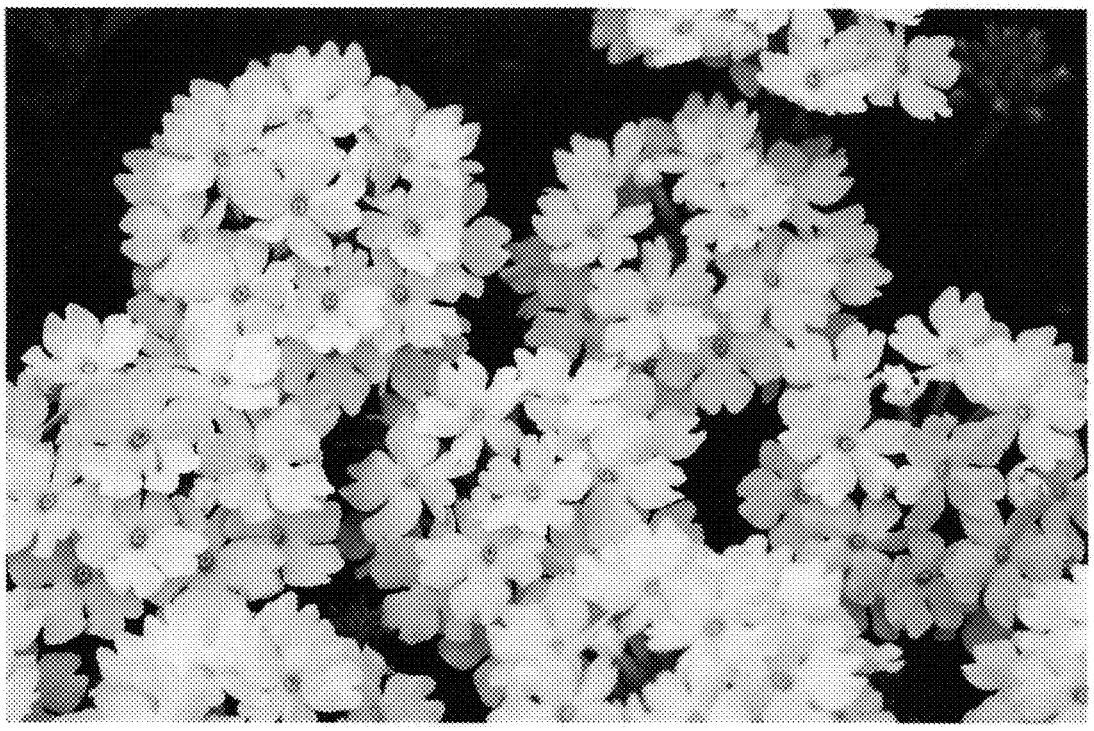

* * * * *